(12) United States Patent  
Schründer

(10) Patent No.: US 6,613,041 B1  
(45) Date of Patent: Sep. 2, 2003

(54) DEVICE FOR DETERMINING THE SURFACE SHAPE OF BIOLOGICAL TISSUE

(75) Inventor: Stephan Schründer, Berlin (DE)

(73) Assignee: Bioshape AG, Berlin (DE)

( * ) Notice: Subject to any disclaimer, the term of this patent is extended or adjusted under 35 U.S.C. 154(b) by 0 days.

(21) Appl. No.: 09/763,270

(22) PCT Filed: Aug. 19, 1999

(86) PCT No.: PCT/DE99/02642

§ 371 (c)(1), (2), (4) Date: Apr. 23, 2001

(87) PCT Pub. No.: WO00/10449

PCT Pub. Date: Mar. 2, 2000

(30) Foreign Application Priority Data

Aug. 20, 1998 (DE) .......................................... 198 37 932

(51) Int. Cl.⁷ ................................................ A61B 18/18
(52) U.S. Cl. ............................................................ 606/5
(58) Field of Search ................................. 600/476, 477, 600/478; 351/205, 211, 212; 378/44, 45, 51, 53; 606/4, 5

(56) References Cited

U.S. PATENT DOCUMENTS

| | | | |
|---|---|---|---|
| 4,573,181 A | * | 2/1986 | Gronberg et al. ............. 378/45 |
| 4,761,071 A | | 8/1988 | Baron |
| 4,799,784 A | * | 1/1989 | Safir ........................... 351/212 |
| 5,634,920 A | | 6/1997 | Hohla |
| 5,701,902 A | | 12/1997 | Vari et al. |

* cited by examiner

*Primary Examiner*—George Manuel  
(74) *Attorney, Agent, or Firm*—Dority & Manning, P.A.

(57) ABSTRACT

The invention is relative to a method for determining the surface form of biological tissue in which the tissue (8a) is directly irradiated with an irradiation pattern (26) produced with the aid of an excitation radiation (2) so that the irradiated tissue areas are excited to emit a fluorescent pattern (27) consisting of fluorescent radiation (14), which pattern is detected and evaluated in order to calculate the surface form of the tissue (8a). A device in accordance with the invention includes at least one radiation source (1) for generating an excitation radiation (2), a device (4) for producing an irradiation pattern from the excitation radiation (2) directly on the tissue (8a) so that the irradiated tissue areas are excited to emit a fluorescent pattern (27) consisting of fluorescent radiation (14), at least one detection device (12) for detecting the fluorescent radiation (14) emitted by the tissue (8a), and an evaluating unit for calculating the surface form of the tissue (8a) from the detected fluorescent radiation (14).

58 Claims, 4 Drawing Sheets

DEVICE FOR DETERMINING THE SURFACE SHAPE OF BIOLOGICAL TISSUE

BACKGROUND

The invention concerns a method and a device for determining the surface form or shape of biological tissue.

The exact knowledge of the topology of biological tissues is in many instances indispensable, e.g., for carrying out operations of the tissue surface. The corneal surface of the human eye is cited as an example. Since the cornea has a power of refraction of above 40 diopters, it is decisive in the refraction of the light falling into the eye and thus participates in the seeing process. The power of refraction thereby is primarily a function of the form of the corneal surface and in particular of its curvature. Modern methods of correcting ametropias therefore aim to alter the corneal form by the removal of corneal tissue with the aid of a laser. Therefore, the prerequisite for a purposeful working of the cornea is the exact knowledge of the form of its outer surface. This is currently determined before and several days after the correction of the ametropia with the aid of optical methods in which the measured values are not appreciably influenced by the statistical and involuntary movements of the eye on account of the rapidity of these methods.

A known method of measuring the corneal form, which is used before or after an ametropic operation or also in order to adapt contact lenses, is based on the use of so-called keratometers, in which the reflection of concentric rings (so-called placido rings) on the tear film that moistens the cornea is recorded with a camera and evaluated. An illuminating device is placed in front of the eye and a disk with circular slits concentric to each other is arranged in front of the device and in whose center a camera is set up. The light reflected from the tear film and recorded by the camera in the form of a ring pattern distorted by the curvature of the cornea is compared in order to determine the specific characteristics of the corneal form to be measured with a given corneal form of a standard eye with a corneal radius of 7.8 mm. In order to reconstruct the surface form of the particular cornea, the user first manually determines the center of the rings, usually approximately 20, with the aid of cross hairs. 180 meridians are then placed through the center over the cornea with an interval of 1° each. The interval of the intersections of the meridians with the rings increases with the growing radius of the rings up to values of approximately 300 µm. Altogether, 180 (meridians)×20 (rings)×2 (intersections)=7200 data points result from which the curvature of the cornea can be calculated. This known method and this known device have the disadvantage that due to the concentric arrangement of the illuminating device and of the camera, no data can be recorded in a surface of the center with a diameter of at least 1.5 mm. However, measurements are especially important particularly in this area. Furthermore, erroneous measurements of a corneal form cannot be avoided which form deviates greater than is customary from the form of a standard eye, such as, e.g., in the case of a central flattening. In addition, the number of 7200 data points is insufficient in some instances for the interpolation necessary to determine the corneal topology. This number of data points effectively represents an upper limit since the meridians cannot be divided at an angular interval of less than 1° on account of their finite width of line.

Since the previously described method and the corresponding device do not permit any monitoring during the removal process, erroneous corrections are recorded relatively frequently, especially in the case of high ametropias above −6 diopters. These erroneous corrections can be evaluated by the user or the operator statistically to prepare so-called "nomograms" that aid in preventing the erroneous corrections in the means in subsequent operative incisions; however, this solution is not adequate.

Moreover, the industrially established so-called strip-projection method for the optical measuring of surfaces of very different types of lifeless materials is known that permits a reliable, contactless and rapid detection of measured values. The basic idea of the strip-projection technique resides in the uniting of measuring-technology possibilities of geometrical-optical triangulation with those of classic interferometry. The mathematical connections are presented in detail in the annex. This method and the corresponding device are particularly suited for detecting rapid events since only a single photograph is necessary. In this method a suitable strip pattern is first projected onto the surface to be measured. The strips are generated by interferometry or by the representation of a suitable structure (grid, etched structure in glass, LCD matrix, micromirror). The light diffusely scattered from the surface in the form of a strip pattern distorted by the surface form of the cornea is detected at an angle a to the direction of projection or irradiation and evaluated by suitable algorithms. The required Fourier transformations that were previously time-intensive no longer constitute an appreciable delay on account of new computer possibilities.

However, the evaluation of the strip patterns becomes problematic given a relatively weak contrast of the detected strip pattern. Phase-measuring errors occasionally occur that make themselves noticeable in jumps in the surface. As is known, contrast-elevating measures consist in vapor-depositing strongly scattering layers on the object or in the addition of fluorescent dyes. The latter has been suggested in particular in ophthalmology, e.g., by Windecker at al. (Applied Optics 43, 3644 ff., 1995) who suggested enriching the tear film in front of the cornea with fluorescein in order to determine the form of the corneal surface in a strip-projection method. In this method, blue light filtered with a filter out of white light is guided onto the cornea, whereupon the tear film located in front and enriched with fluorescein emits green light as a consequence of the excitation. U.S. Pat. No. 5,406,342 teaches a similar method (and a corresponding device) in which the superpositioning of two partial patterns projected from two directions onto the cornea provided with fluorescent liquid results in the production of a moire pattern that can be evaluated. The fluorescent radiation emitted by the liquid film is combined after having passed through an optical filter by the successive recording of two half images with a video camera and evaluated by specially developed algorithms. The projection of the radiation from two directions helps, in addition to the filter, to avoid the detection of the direct reflex that is produced at the location on the cornea whose surface normal divides the angle between the direction of radiation and the direction of observation into two equally large angles and always appears when the detection unit is sensitive to the wavelength projecting the pattern.

Other methods and devices for determining the corneal topography in which a fluorescent agent is applied onto the eye are known from U.S. Pat. No. 4,995,716; U.S. Pat. No. 4,761,071 and U.S. Pat. No. 5,159,361.

These known methods and devices have the disadvantage that the tear film always exhibits locally and individually different thicknesses so that conclusions about the surface of the cornea can not be reliably drawn from measuring it. Since the fluorescent agent continues to be distributed in the tear film and thus supplies scattered light from the entire thickness of the tear film, the measuring accuracy can not be greater than the film thickness, that amounts up to 200 $\mu$m. Furthermore, the liquid would penetrate into the corneal tissue if the epithelial layer on the cornea were not present or folded back out of the radiation path, which would result in a widening of the depth resolution. Moreover, in such an instance the surface form of the cornea would change since it swells up. Thus, an intact epithelial layer is necessary for the use of this known method or this known device; however, it is precisely this layer that must be removed before an operation, so that measurements during an operation, for example, are not possible.

Moreover, GB-A-2,203,831 teaches a device for investigating tumors with fluorescent radiation. To this end the tissue (tumor) to be investigated is irradiated by a light source that emits light in the UV range. The tissue is excited as a consequence thereof to emit fluorescent radiation that is detected by a detection system and subsequently measured. However, the known device is only suited for investigating the tissue qualities of biological tissue such as tumors but not for determining the surface form of biological tissue.

SUMMARY OF THE INVENTION

Objects and advantages of the present invention will be set forth in the following description, or may be obvious from the description, or may be learned through practice of the invention.

The present invention addresses the problem of further developing a device of the initially cited type in such a manner that the topology of a biological tissue can be determined in a simple manner and in the absence of any liquids, in particular fluorescent liquids, and that the results can possibly be used for operative treatment.

This problem is solved in the method according to this invention of the initially cited type in that the tissue is directly irradiated with an irradiation pattern produced with the aid of an excitation radiation so that the irradiated tissue areas are excited to emit a fluorescent pattern consisting of fluorescent radiation, which pattern is detected and evaluated in order to calculate the surface form of the tissue.

Furthermore, the problem is solved in a device according to this invention wherein the radiation source generates an excitation radiation with a wavelength located substantially in the ultraviolet (UV) wavelength range.

The advantages of the invention can be seen in particular in the fact that no film located in front of the biological tissue and enriched, if necessary, with a suitable substance is excited to the omission of fluorescent radiation but rather the biological tissue itself is. To this end, the intensity, and in particular the wavelength of the excitation radiation, is selected in such a manner that its penetration depth into the tissue is low and actually only the outermost tissue areas (e.g., 2–3 $\mu$m) are excited to fluorescence. The fluorescent pattern to be detected corresponds thereby substantially to the radiation pattern projected previously onto the tissue, distorted by the possibly curved surface of the tissue to be measured as well as by the angle between the detection of observation and the direction of radiation. The non-irradiated tissue areas are not excited thereby to the emission of fluorescent radiation. Since an undesired spatial distribution of fluorescent material, such as, e.g., in the case of a fluorescent film of liquid on the tissue, does not occur, no measuring inaccuracies occur as a result. Likewise, a swelling up of the tissue due to such a film of liquid located in front is avoided.

Especially in the instance of the cornea, fluorescent liquids or liquids marking in another manner to be applied onto the eye can be eliminated in the case of the method and device in accordance with the invention. It is thus possible in a surprisingly simple manner to directly represent the corneal surface by fluorescent radiation without having to take the imprecise detour via a fluorescent film located in front.

According to the invention, the radiation source generates an excitation radiation with a wavelength located substantially in the ultraviolet wavelength range. In this instance the UV radiation penetrates only a few micrometers into the cornea (the cornea is transparent above the UV wavelength range up to the near infrared (IR)). Consequently, the fluorescent radiation emitted from the cornea stems substantially from the outermost tissue layer and thus represents its topology in a sufficiently exact manner. Furthermore, the measuring can take place in a sufficiently short time to avoid erroneous measurements due to eye movements. By means of the method and the device according to the invention it is also possible to measure, e.g., deformations of extremities or changes of the skin surface and other structural features of the skin (e.g., fingerprints). Beforehand, it may be necessary to remove disturbing objects in the optical path from the tissue surface, e.g., hairs. The form of the surface of the tissue to be measured can basically be shaped in any way; however, no coarse graduations should be present.

The evaluating unit for evaluating the fluorescent pattern of the fluorescent radiation preferably comprises a computer with a suitable analyzing software that uses, e.g., known mathematical methods. Such a known mathematical method for evaluating the fluorescent radiation is given in the annex.

Since the method and the device of the invention are based on the fluorescent qualities of the tissue itself, the method is also particularly suitable for detecting the topology during the refractive operation on the cornea during which no tear film and no epithelial layer, at least in the radiation path of the excitation radiation, is present. For example, the instantaneous tissue topology is determined sufficiently often before and during operation so that the next operation step can be coordinated with the actual result. This thus permits the controlling/regulating of the removal process during the operation with a laser, for example, in that one can switch between operating mode and the mode for determining the surface form of the cornea, so that a more exact correction is possible than previously as a result of the constant monitoring and the corresponding reacting. As a result thereof, even nomograms individually determined by the user from statistical investigations become superfluous, which were still necessary up to the present, especially in the case of large corrections above –6 diopters.

It is especially preferable if the radiation source for determining the surface form of the biological tissue and that for the operative treatment of the tissue are identical. In this manner, a compact and relatively inexpensive device for determining the tissue topology and the operation of the tissue can be realized. In this manner, very precise tissue corrections can be carried out rapidly and simply with the aid of the method and device of the invention. The problem is therefore also solved in a method for supporting an operative intervention on a biological tissue in that the result of the evaluation is included in a regulating and/or controlling manner in the actual operative treatment of the biological tissue.

Furthermore, it is advantageous if the detection of the fluorescent radiation can take place with a device whose sensitivity for the excitation wavelength is a priori very low on account of the wavelength difference between the excitation radiation and the fluorescent radiation. A CCD camera that permits a locally resolved detection can be used to this end. If necessary, a camera sensitive in the ultraviolet range can also be used. Additionally or alternatively, the sensitivity of the particular detection device for the excitation wavelength can be reduced by a filter (color filter or polarization filter). In this manner, the direct reflex does not appear in a disturbing manner during the detection. It can not be avoided, just as in the known methods and devices. However, it is not detected on account of the sensitivity of the detection device located in another wavelength range and can therefore not cover over the desired signal. Thus, only a single exposure is required for the complete reconstruction of the surface of the biological tissue.

The fluorescent radiation emitted by the biological tissue is preferably detected at an angle different from the direction of the radiation which angle is, e.g., 45°. In this manner the fluorescent pattern is observed in a perspectively distorted manner so that, in particular, a curvature of the tissue surface can be measured in a more precise fashion. For example, the adjacent strips of a fluorescent-strip pattern appear more curved in such an observation on account of the perspective than in a frontal observation, for which reason more precise information about the course of curvature can be obtained.

If the direct fluorescent radiation is caught solely with a single detection device and the direction of irradiation and the direction of observation do not coincide, a perspectively distorted image of the fluorescent pattern is obtained, as discussed. Therefore, in the case of a very fine irradiation pattern and therewith fluorescent pattern that makes possible a very fine resolution of the tissue topology, lines located in the areas facing away from the direction of detection coalesce in an undesired manner and can then no longer be precisely resolved. Therefore, at least one further detection device can advantageously be used which is opposite, relative to the direction of irradiation, the first detection device and serves to detect the fluorescent radiation from a range of the biological tissue that cannot be precisely detected by the first detection device. Alternatively, a mirror suitably positioned in front of the biological tissue can also be used that reflects the fluorescent radiation from the side of the biological tissue facing away from the (single) detection device to this latter detection device. In this manner, e.g., two spatial half images can be recorded simultaneously (with two detection devices) or successively (with one detection device and one mirror) and appropriately combined for evaluation.

Additionally or alternatively, the biological tissue is irradiated from at least two directions in order to sufficiently detect tissue areas that are otherwise difficult to illuminate on account of the perspective distortion. It is advantageous to provide a symmetrical design of the device of the invention for this when measuring a cornea, in which instance, e.g., the two directions, one of projection and one of irradiation, enclose the same angle with a direction of observation running between them. Also, in addition to using several radiation sources, the use of several detection devices can be provided. Likewise, mirrors or other light deflection devices are available for illuminating and/or irradiating the biological object from several sides.

The biological tissue, and in particular the cornea, are preferably excited to fluorescence with wavelengths between 150 nm and 370 nm. Wavelengths shorter than approximately 150 nm can currently be generated with sufficient energy only with a high technical expense. Moreover, they generate a fluorescent radiation that would be difficult to detect with conventional technology on account of their wavelength, which is likewise only slightly longer. Wavelengths longer than approximately 370 nm, on the other hand, exhibit, at least in the case of the cornea for visible light, too great a penetration depth to limit the emission of fluorescent radiation to the outermost cellular layers and therewith assure the required precision of measurement. In addition, damage to the eye could occur in this special case.

Since the eye makes involuntary movements, so-called saccades, during the measuring of the cornea, it is advantageous to appropriately limit the irradiation time, preferably below 20 ms, since the detected fluorescent pattern could otherwise be distorted. New laser devices are capable of emitting pulses on the magnitude of femtoseconds, that can also be used if necessary.

The cited problem of the obligatory limitation of the irradiation time due to the eye movements can be circumvented in the method and with the device in accordance with the invention by the use of at least one eye tracker, with which longer irradiation times can be realized. The eye tracker records the courses of the movements of the eye, preferably during the irradiation, as a function of the time, that are included during the evaluation of the fluorescence pattern. The excitation radiation is readjusted with respect to the eye by means of the information obtained in this manner in order to realize longer irradiation times.

Furthermore, a determination of the position of the eye with an eye tracker that can absolutely correspond to the eye tracker indicated above is preferably provided before each irradiation with the irradiation pattern and after each detection of the fluorescent pattern. It is additionally or alternatively provided to the above that the position of the eye is determined during the irradiation with the irradiation pattern and during the detection of the fluorescent pattern with an eye tracker. The irradiation or detection is halted upon a change of the position of the eye during the irradiation with the irradiation pattern or during the detection of the fluorescent pattern and a new irradiation of the cornea of the eye with subsequent detection of the fluorescent pattern is carried out.

It turned out to be advantageous if the irradiation pattern is cast in short time intervals onto the tissue. A sufficient fluorescent intensity with simultaneous protection of the tissue from light-induced removal is realized with such an irradiation pulse series. In the case of rapidly switching optical elements, several hundred irradiation pulses can be applied within the given flash time. The repetition rate for each measurement, that is composed of an irradiation with subsequent detection of the fluorescent pattern, is preferably between 1 Hz and 1 MHZ.

In order not to permanently damage corneal tissue or other biological tissue by the excitation radiation, the projection of the geometric irradiation pattern is carried out with a sufficiently low fluence (energy/surface). This fluence should be less than 10 mJ for a circular surface area with a diameter of 10 mm. Likewise, phototoxic effects are avoided therewith. The energy of the excitation radiation is preferably between 1 $\mu$J and 1 J.

The radiation exciting the fluorescence is emitted, e.g., by an excimer laser, that is also used for the operative work on the cornea. For example, an ArF laser with a wavelength of 193 nm is used. Alternative laser devices that permit the emission of radiation pulses are, in addition to excimer lasers (ArF with a wavelength of $\lambda=193$ nm, KrF with $\lambda=248$ nm, XeCl with $\lambda=308$ nm, XeF with $\lambda=351$ nm) and nitrogen lasers ($\lambda=337$ nm), also frequency-multiplied solid lasers (Nd YAG 5-fold with $\lambda=213$ nm and 4-fold with $\lambda=266$ nm and 3-fold with $\lambda=355$ or alexandrite) or dye lasers pumped by such solid lasers. It is advantageous to select a wavelength at which the intensity of the fluorescent radiation is as high as possible since the demands on the detection device drop as a result thereof.

An alternative to a laser is the use of more economical flash lamps filled with gaseous mixtures containing xenon or deuterium. These lamps are preferably limited by suitable filters to the emission of UV radiation. Since the output performance of these flash lamps in the UV range is usually lower than those of lasers, higher requirements must be placed on the detection device if necessary.

The geometric irradiation pattern projected onto the biological tissue such as, e.g., the cornea, preferably consists of parallel strips with a sinusoidal, $\cos^2$, or square intensity course. The surface can be measured with a resolution of a few micrometers therewith, e.g., at a strip width and a strip interval of 100 $\mu$m with suitable algorithms. Alternatively, a grid whose intersections are used for the evaluation, a perforated pattern, a pattern consisting of several concentric circular lines with lines emanating radially from the center and with lines arranged with the same angular interval, a moire pattern consisting of two line patterns or some other geometric pattern can be selected.

The means for producing the geometric irradiation pattern preferably comprise a mask with, e.g., parallel slits or regularly arranged perforations that are reproduced by irradiation on the tissue. The intensity losses are relatively slight in these patterns, which is particularly advantageous in irradiation systems with relatively low output.

As an alternative, substrates (e.g., glass) altered structurally areawise by suitable preparation can be used as means for producing the irradiation pattern. Such substrates, for example, may have areas of strong scatter or absorption alternating with unprepared areas of high transmission. Such substrates permit the generation of a sinusoidal intensity course.

The irradiation pattern can also be generated in an advantageous manner by known diffractive, optical elements such as, e.g., microlenses. The microlenses, whose diameter is, e.g., 100 $\mu$m, are applied, e.g., in a close, regular arrangement on a transparent glass substrate that is placed in the radiation path of the excitation radiation exhibiting, e.g., a ray diameter of 8 mm. If the individual microlenses are designed as cylindrical lenses, strip patterns can be generated in this manner. Even other lens forms, e.g., semicircular, are possible and define a different irradiation pattern and therewith different fluorescent pattern. The microlenses permit the achievement of a greater depth sharpness, that is advantageous in the case of the curved cornea. In addition, the energy of the excitation radiation is better utilized than when using a mask, that does not allow a part of this radiation to reach the eye. Furthermore, a more precise sinusoidal intensity course of, e.g., alternating bright and dark strips can be generated than in the case of a mask.

Alternatively, the irradiation pattern can also be produced on the biological tissue by interference in that the radiation, that is widened out, if necessary, is sent from a monochromatic, coherent radiation source (laser) through a beam splitter and is recombined and united on the biological tissue. Alternatively, an interference pattern can be produced on the tissue by two radiation sources coordinated with one another with radiation coherent to one another.

The irradiation pattern can also be produced by a field of micromirrors on which the excitation radiation is reflected to the tissue in a suitable manner. Such mirrors are characterized by short adjustment times and the generation of individual irradiation patterns. For example, 300×400 micromirrors are arranged uniformly adjacent to each other.

The irradiation pattern produced on the biological tissue can be composed of several partial patterns generated in one or several of the above-mentioned ways.

The structured fluorescent radiation is preferably recorded with a sufficiently sensitive CCD camera with high spatial resolution (high pixel number, e.g., 1280×1024 pixels) that makes possible a site-resolved detection of the fluorescent pattern (a site-resolved detection is especially advantageous on account of the relative simplicity of the evaluation as well as its precision). Several hundred thousand evaluatable data points can be obtained in this manner. In addition, if the excitation radiation is in the UV range and the fluorescent radiation is in the visible range, a CCD camera is also advantageous because its sensitivity in the visible wavelength range is greater than in the ultraviolet range. In addition, the camera lens of customary CCD cameras acts as a band-pass filter for wavelengths above 300 nm, so that fluorescent radiation above this wavelength is detected and not, in contrast thereto, the excitation radiation reflected from the tissue, if the latter is located in the shorter-wave UV range.

The CCD camera can be connected to an amplifier in the case of relatively weak radiation intensities, as well as when using flash lamps.

Advantageous further developments of the invention are set forth in the appended claims.

BRIEF DESCRIPTION OF THE DRAWINGS

An exemplary embodiment of the invention is explained in detail in the following with reference made to the drawings.

DESCRIPTION

Reference will now be made in detail to one or more embodiments of the invention, examples of which are shown in the figures. The embodiments are presented by way of explanation of the invention, and not meant as a limitation of the invention. Modifications and variations can be made to the embodiments described herein without departing from the scope and spirit of the invention as set forth in the appended claims.

Figure 1:
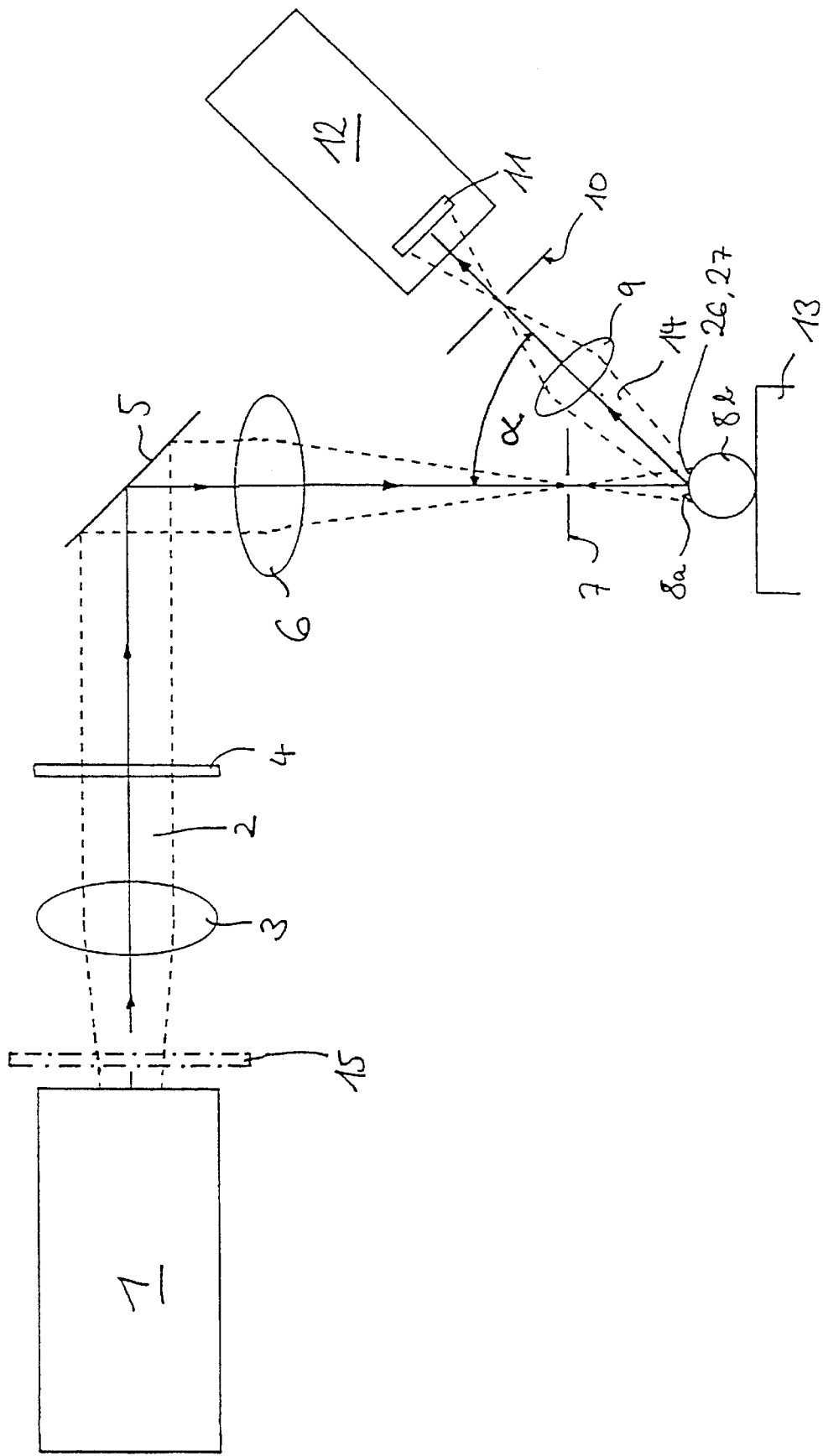
FIG. 1 shows a schematic design of a first embodiment of a device for projecting an irradiation pattern onto a cornea and for detecting the fluorescent pattern produced.

FIG. 1 shows a first embodiment of the device in accordance with the invention. Radiation source 1 generates excitation radiation 2, preferably an UV radiation. Since the latter is not necessarily collimated, an optional, first lense system 3 (indicated by a schematically represented converging lens) assures a parallel and homogeneous beam. This beam passes through means for producing irradiation pattern 26, which means is formed in the embodiment shown by slotted diaphragm or mask 4 positioned vertically to the beam path and with, e.g., parallel, strip-shaped openings with a width and an interval of 100 μm (not shown). Excitation radiation 2, of which FIG. 1 shows only the center beam as a solid line with indication of the direction of radiation as well as the outlines or edge beams as dotted lines, is partially retained at this mask 4 and partially let through by the openings. In this manner, excitation radiation 2 is structured transversely to the direction of radiation in the form of irradiation pattern 26, which is deflected in the further course of the beam on mirror 5 and imaged by a second lens system 6 (indicated by a schematically represented converging lens), after having passed through a first aperture diaphragm 7, on the surface of biological tissue 8a. Tissue 8a in the selected exemplary embodiment is, e.g., eye cornea 8a of a human patient placed on patient support 13 (for the sake of simplicity only eye 8b of the patient is shown).

Excitation radiation 2 passing mask 4 is selected with respect to intensity and wavelength in such a manner that it penetrates only a few micrometers into cornea 8a. This is the case, for example, when its wavelength is located in the UV range. Excitation radiation 2 excites cornea 8a to emit fluorescent radiation 14 in the irradiated areas whereas the non-irradiated areas of cornea 8a cannot emit any fluorescent radiation 14. In this manner, cornea 8a emits fluorescent pattern 27 corresponding to irradiation pattern 26 and distorted by the corneal curvature, which pattern is imaged on sensor 11 of detection device 12 at an angle a with the aid of a third lens system 9 after having passed through a second aperture diaphragm 10. Detection device 12 is, e.g., a CCD camera optionally intensified by an image intensifier (not shown). One exposure by detection device 12 suffices to obtain all the information required about the surface form of the cornea. To this end, detection device 12 is connected to an evaluating unit (not shown) preferably constituted by a computer that calculates the form of cornea 8a with the aid of evaluation programs.

The wavelength of excitation radiation 2 is, e.g., approximately 193 nm, when using an ArF laser as radiation source 1. A frequency-quintupled Nd:YAG laser that is also used with preference emits excitation radiation 2 with a wavelength of 213 nm. The main maxima of fluorescent radiation 14 emanating from the irradiated tissue areas of cornea 8a are located in these instances at approximately 300 nm and 450 nm, which are accessible to detection without significant expense, such as, e.g., with CCD camera 12.

If possible, no tear film should be present on cornea 8a in order to prevent an absorption of excitation radiation 2 by the tear film. This necessity agrees very well with the conditions necessary during an operation on cornea 8a, that is generally carried out on eye 8b free of a tear film. The method and device presented are therefore suitable in particular for the combination of alternately measuring the form of cornea 8a and its operative treatment, which is advantageously performed with the same radiation source 1, usually a UV laser. The results of the determination of the corneal form can then be used immediately in the following operation step in order to control and regulate the removal of cornea by the laser. During a subsequent measuring phase the result of the preceding operative step can be monitored immediately and the next operation step coordinated with it. This alternating process is preferably controlled automatically by a computer.

During the use of a laser beam that is capable of removing cornea 8a over a large area, at least one intensity attenuator 15 (shown in dotted lines in FIG. 1) is inserted into the beam path of excitation radiation 2, that is, between radiation source 1 and cornea 8a, during the measuring of the corneal surface in order to protect cornea 8a. This intensity attenuator is removed out of the beam path during the operation phases. The inserting and removal of intensity attenuator 15 into and out of the beam path are preferably performed in a computer-controlled manner.

In another embodiment (not shown) a laser beam with a diameter of, e.g., 2 mm is used to remove cornea 8a in only small areas. To this end, the laser beam is conducted in a scanning fashion over cornea 8a. Therefore, during the measuring of the corneal surface, the laser beam must be widened with at least one beam widener (not shown) in order to produce irradiation pattern 26 with a greater surface area, which beam widener is introduced between radiation source 1 and cornea 8a into the beam path. During the operation phases, the at least one beam widener is removed again from the beam path of excitation radiation 2.

Figure 2:
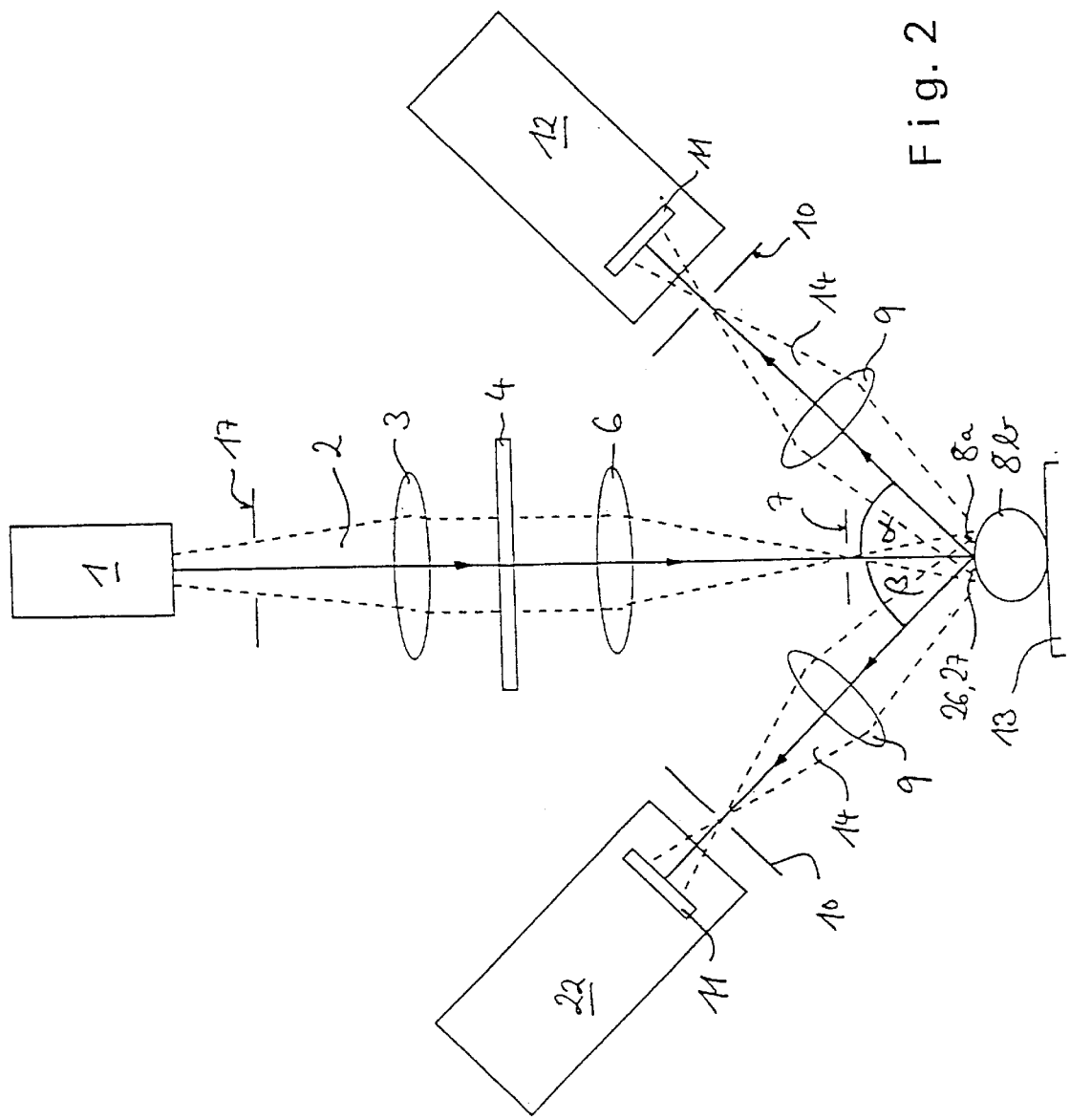
FIG. 2 shows a schematic design of a second embodiment for pattern projection and pattern detection.

In the second exemplary embodiment of the device shown in FIG. 2, two detection devices 12, 22 are arranged opposite one another in front of cornea 8a. The directions of observation, illustrated by the particular central connecting lines between cornea 8a and detection devices 12, 22, form in the instance shown the equally large angles α, β with the direction of irradiation, that coincides with the central beam of excitation radiation 2. In this exemplary embodiment, radiation source 1 is located directly opposite cornea 8a. In analogy with the first exemplary embodiment according to FIG. 1, irradiation pattern 26 falls, after passing a third aperture diaphragm 17, the first lens system 3, the means 4 for generating irradiation pattern 26 as well as the second lens system 6, onto cornea 8a of human eye 8b. Fluorescent radiation 14 of fluorescent pattern 27 is detected in this exemplary embodiment after passing through third lens systems 9 and second aperture diaphragms 10 from two sides in order to obtain a higher resolution. In this manner, given a curved tissue surface, even the tissue side facing away from the particular detection device 12, 22 can be determined in a precise topographic manner with the particular other detection device 22, 12. If, e.g., irradiation pattern 26 is formed by regularly arranged, spaced circles lying on the intersection points of an imaginary square grid, the circles draw together on account of the perspective distortion on the side facing away from detection device 12 until they can perhaps even no longer be resolved. This tissue area can then be precisely detected by detection device 22 located opposite it. The same applies, with exchanged roles, to the tissue area facing away from detection device 22.

In another embodiment (not shown), tissue 8a is irradiated from two directions. For example, a beam splitter splits excitation radiation 2 from radiation source 1 and directs it with the aid of one or several light deflection devices such as, e.g., mirrors, onto tissue 8a. Alternatively, several radiation sources 1 are used. Such a design might look, e.g., like the one in FIG. 2, only the two detection devices 12, 22 in FIG. 2 would have to be replaced by two radiation sources 1 and radiation source 1 in FIG. 1 by detection device 12. Naturally, means 4 for generating irradiation pattern 26 as well as lens systems 3, 6, 9 and aperture diaphragms 7, 10, 17 would also have to be appropriately repositioned.

Figure 3:
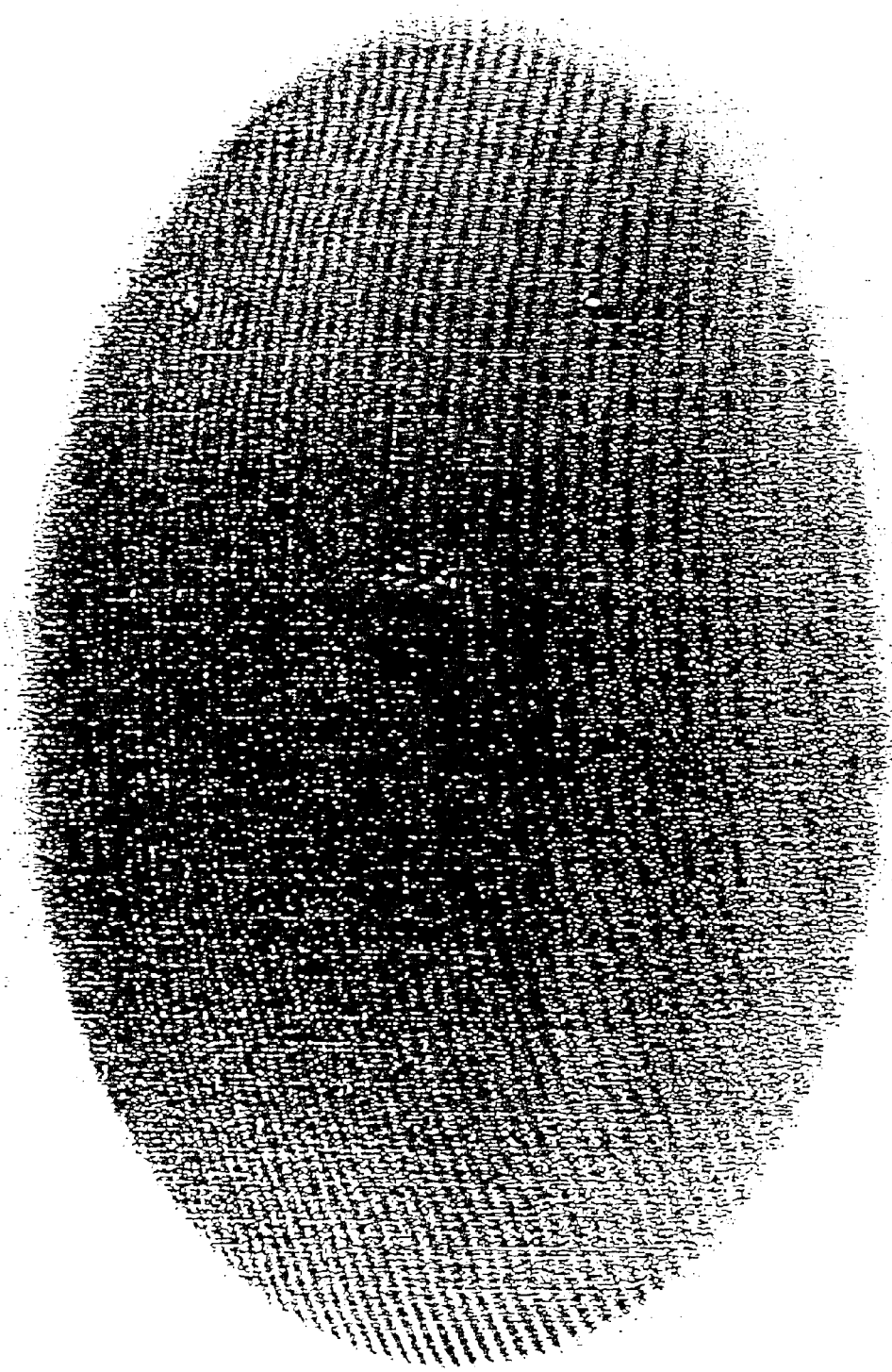
FIG. 3 shows a fluorescent pattern observed on an eye cornea with a CCD camera which pattern was generated by irradiating the cornea with an appropriate irradiation pattern according to FIG. 1.

FIG. 3 shows inverted, strip-shaped fluorescent pattern 27 recorded by CCD camera 12 which pattern was detected during the irradiation of cornea 8a with a strip-shaped irradiation pattern 26 in accordance with the test design of FIG. 1. Irradiation pattern 26 was generated here with the aid of an ArF excimer laser (λ=193 nm) and of mask 4 with parallel openings and projected only on the central area of cornea 8a that corresponds to the area that is customarily treated during a laser operation, that is, that is to be removed in different thicknesses. The energy striking cornea 8a was approximately 2 mJ in this instance whereas the laser beam had a diameter of 8 mm. The non-illuminated adjacent areas 18 directly adjacent to this area are likewise part of cornea 8a. If necessary, a digital subtraction of the images recorded before and during the irradiation of irradiation pattern 26 can increase the contrast and therewith the precision of the method even more.

No externally applied liquid film or tear film was on cornea 8a during the recording of fluorescent pattern 27 shown in FIG. 3; the uppermost layers of cornea 8a were excited in the areas irradiated with irradiation pattern 26 directly to the emission of fluorescent radiation 14 with the aid of excitation radiation 2. In addition, the epithelial layer on cornea 8a had been previously removed. Alternatively, the epithelial layer is folded back out of the beam path of the excitation radiation after an appropriate scratching with a part of the stroma located under it and is brought back into its original position after the operation.

The strips drawing closer together at the top in FIG. 3 are a consequence of the perspective distortion on account of the direction of observation regarding eye 8b, which direction is inclined in comparison to the direction of irradiation (see FIG. 1; there the tissue side facing detection device 12 corresponds to the lower area of fluorescent pattern 27 in FIG. 3 whereas the tissue side facing away from detection device 12 corresponds to the upper range of fluorescent pattern 27).

Whereas the exemplary embodiments cited above were explained regarding the measuring of the surface form of an eye cornea, the method and the device in accordance with the invention are also suitable without limitation for being used in a corresponding manner on other biological tissues.

Supplement

The essential mathematical interrelationships are explained in the following with reference made to FIG. 4 that are used for the evaluation of the emitted fluorescent radiation in a strip pattern (the irradiation pattern) projected onto a biological tissue 8a. Arrows x and y in FIG. 4 indicate the direction of irradiation and the direction of observation. The strip interval produced on the object or tissue 8a is designated with p. Magnitude d is the interval of the strips as it is perceived by the observer under the angle α. The effective wavelength, that is one of the important magnitudes in the evaluation of the strip pattern, is designated with $\lambda_{eff}$.

Figure 4:
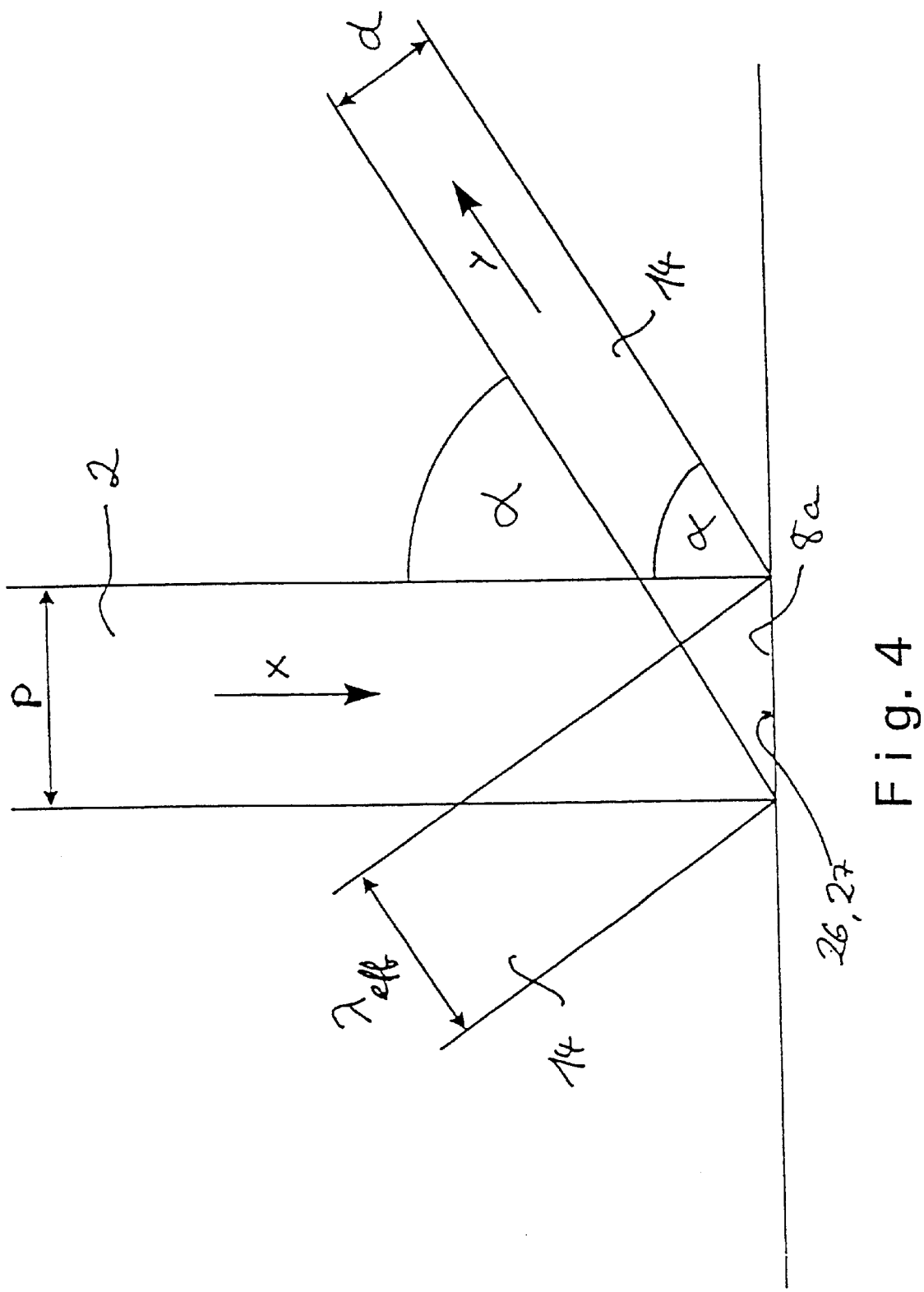
FIG. 4 shows a simplified view of the beam courses (to explain the mathematical derivations given in the annex).

An important magnitude is the interval of the strips vertically to the direction of observation, that is also designated as the effective wavelength $\lambda_{eff}$ and can be calculated in accordance with FIG. 4 according to the following formula:

$$\lambda_{eff} = p/\sin\alpha = d/\tan\alpha = \beta L/\sin\alpha \tag{1}$$

In equation 1, α is the angle between the direction of irradiation and the direction of observation. L is the strip interval on the irradiation pattern imaged via lens system 6 with enlargement factor β on the surface of the object or tissue 8a. Magnitude d is the strip interval from the perspective of the observer.

The effective wavelength $\lambda_{eff}$ is, analogously with interferometry, an important magnitude according to which the sensitivity of the system is determined. It is apparent from equation 1 that $\lambda_{eff}$ can be varied by varying angle α and strip interval L. The elevation resolution is up to λ/100, depending on the projection method used.

If a projection grid with a $\cos^2$-shaped intensity course is used, an intensity structure I (x,y) is produced by its projection on the surface of the measured object or tissue 8a which intensity structure can be described by equation 2:

$$I(x,y) = I_0(x,y) + V(x,y) \cos \phi(x,y) \tag{2}$$

In this equation $I_0$ (x,y) is the background intensity, V (x,y) the strip contrast and φ (x,y) the interference phase relationship. The phase term φ (x,y) represents the connection between the parallel strip lines and the contour course of the surface of the object or of tissue 8a. The contour course results quantitatively from equations 1 and 2 in $$z(x,y) = [\phi(x,y)\lambda_{eff}]/4\Pi \tag{3}$$

According to equation 3 a rapid and precise measuring of the phase in order to determine the contour course is indispensable. A number of effective phase measuring methods are available from real-time interferometry that solve this problem on the basis of equation 2.

Evaluation methods designated as phase-shift methods are based on the fact that a gradual, defined change of the phase relationship is carried out for precisely one period in the strip pattern by changing optical parameters over the entire image. This takes place, for example, by shifting the reference mirror of an interferometer or by shifting the projection grid. This measuring method yields an accuracy of up to 1/100 of the wavelength used. However, it is characterized by a technical complexity that can often be realized only with difficulty and by a longer measuring and evaluation process in comparison to individual image projection and individual-image evaluation.

It is therefore advantageous if the phase determination requires only one exposure. Spacial heterodyne- or carrier-frequency methods are used for this in real-time interferometry. A local carrier frequency $f_0$ is impressed on the signal thereby, so that equation 2 is changed into:

$$I(x,y) = I_0(x,y) + V(x,y) \cos \{2\Pi i\, f_0 x + \phi(x,y)\} \tag{4}$$

With equation $$c(x,y) = \tfrac{1}{2} V(x,y) \exp\{i\phi(x,y)\} \tag{5}$$

equation 4 results in $$I(x,y) = I_0(x,y) + c(x,y) \exp\{2\Pi i\, f_0 x\} + c^*(x,y) \exp\{-2\Pi i\, f_0 x\} \tag{6}$$

In the above, * signifies complexly conjugated.

The function c (x,y) is obtained therefrom via a Fourier transformation and a back transformation after filtering. The phase then results as $$\phi(x,y) = \tan^{-1}\{Im[c(x,y)]/Re[c(x,y)]\} \tag{7}$$

Here, "Im" is the imaginary part and "Re" the real part of the complex function c (x,y).

What is claimed is:

1. A method for determining the surface shape or form of biological tissue, comprising directly irradiating the tissue with excitation radiation from a radiation source in a predetermined irradiation pattern such that irradiated areas of the tissue are excited to emit a measurable pattern of fluorescent radiation; and detecting and evaluating the pattern of fluorescent radiation to calculate the surface form or shape of the tissue.

2. The method as in claim 1, wherein said step of directly irradiating tissue comprises irradiating one of a cornea of an eye or skin on a finger tip.

3. The method as in claim 2, further comprising detecting eye movement that occurs during said step of directly irradiating the cornea and using the eye movement information to adjust the excitation radiation.

4. The method as in claim 3, further comprising determining the position of the eye before said direct irradiating step, during said irradiation step, and after each detection of the fluorescent pattern.

5. The method as in claim 2, further comprising detecting the position of the eye before said irradiation with the irradiation pattern and after each said detection of the fluorescent pattern.

6. The method as in claim 2, further comprising detecting the position of the eye during said irradiation with the irradiation pattern and during said detection of the fluorescent pattern, and halting said irradiation or said detection upon a change of position of the eye and adjusting subsequent said irradiation of the eye based on the changed eye position.

7. The method as in claim 1, wherein said step of directly irradiating tissue comprises irradiating a cornea of an eye, said method further comprising removing a tear film from the cornea prior to said irradiating.

8. The method as in claim 7, further comprising removing an epithelial layer of the cornea out of a beam path of the excitation radiation prior to said irradiating such that stromal tissue located under the epithelial layer is directly irradiated with the excitation radiation in the predetermined irradiation pattern.

9. The method as in claim 1, wherein said step of directly irradiating the tissue comprises irradiating the tissue with an excitation radiation within the ultraviolet (UV) wavelength range.

10. The method as in claim 1, wherein said step of directly irradiating the tissue comprises irradiating the tissue from at least two directions with the excitation radiation.

11. The method as in claim 1, wherein said step of detecting the pattern of fluorescent radiation comprises using at least one detection device.

12. The method as in claim 11, comprising using a CCD camera detection device.

13. The method as in claim 1, wherein said step of detecting the pattern of fluorescent radiation comprises detecting the radiation at an angle of reflection from the tissue that is different from an incident angle of the excitation radiation on the tissue.

14. The method as in claim 1, further comprising diverting the fluorescent radiation from the tissue to a detecting device with a light diverting device.

15. The method as in claim 1, wherein said step of directly irradiating the tissue comprises irradiating the tissue with excitation radiation within a wavelength range of about 150 nm to about 370 nm.

16. The method as in claim 1, wherein said step of directly irradiating the tissue comprises irradiating the tissue with emission times greater than about 1 femtosecond.

17. The method as in claim 1, wherein said step of directly irradiating the tissue comprises irradiating the tissue with the irradiation pattern and an associated subsequent said detection of the fluorescent pattern at a repetition rate between about 1 Hz and about 1 MH.

18. The method as in claim 1, wherein said step of directly irradiating the tissue comprises irradiating the tissue with an excitation radiation having an energy of between about 1 $\mu$J and about 1 J.

19. The method as in claim 1, wherein said step of directly irradiating the tissue comprises irradiating the tissue with one of a laser or a flash lamp.

20. The method as in claim 1, wherein said step of directly irradiating the tissue comprises irradiating the tissue with a laser from the group consisting of a frequency multiplied solid laser, and excimer laser, a gas laser, a frequency multiplied dye laser, and a frequency multiplied ion laser.

21. The method as in claim 1, wherein said step of directly irradiating the tissue comprises irradiating the tissue with a flash lamp containing a gaseous xenon mixture or a gaseous deuterium mixture.

22. The method as in claim 1, comprising irradiating the tissue with at least one irradiation pattern from the group of patterns consisting of parallel strips, a rectangular grid, a perforated pattern, a moire pattern consisting of two line patterns, and a pattern of concentric circular lines with radial lines emanating from the center thereof at a uniform angular interval.

23. The method as in claim 22, comprising producing the irradiation pattern at least partially by optical imaging with a mask having the pattern defined therein.

24. The method as in claim 1, comprising generating the irradiation pattern at least partially by optical imaging of a structured glass having areas that are essentially transparent to the excitation radiation and areas that scatter or absorb the excitation radiation to define the irradiation pattern.

25. The method as in claim 1, comprising generating the irradiation pattern at least partially by dividing and subsequently combining the excitation radiation from the radiation source.

26. The method as in claim 1, comprising generating the irradiation pattern by combining radiation from two radiation sources to define the excitation radiation.

27. The method as in claim 1, comprising generating the irradiation pattern at least partially with diffractive optical elements.

28. The method as in claim 27, comprising generating the irradiation pattern with at least one lens.

29. The method as in claim 1, comprising generating the irradiation pattern at least partially with an arrangement of mirrors.

30. The method as in claim 1, wherein said evaluating step comprises calculating the surface form or shape of the tissue with an evaluating unit that controls a laser in response to the calculated form or shape, the laser being the radiation source generating the excitation radiation.

31. The method as in claim 30, further comprising reshaping the tissue with the same laser.

32. The method as in claim 1, wherein said step of directly irradiating tissue comprises irradiating a cornea of an eye, and further comprising reshaping the cornea of the eye in a subsequent operative treatment based upon the shape or form of the cornea determined in said evaluating step.

33. The method as in claim 32, wherein said irradiating the cornea and said reshaping of the cornea is done with a UV laser.

34. The method as in claim 33, further comprising placing at least one of a beam intensity attenuator or beam expander device between the UV laser and the cornea of the eye during said irradiating with excitation radiation, and subsequently removing the device during said operative treatment to reshape the cornea with the UV laser.

35. An apparatus for determining the surface form or shape of biological tissue, said apparatus comprising:
- at least a first radiation source configured for generating an excitation radiation having a wavelength generally with the UV wavelength range;
- an irradiation pattern generating device disposed downstream of said radiation source to project said excitation radiation directly onto the biological tissue in a desired irradiation pattern, the biological tissue being excited by the excitation radiation to emit a corresponding fluorescent irradiation pattern;
- at least one detection device disposed to detect the fluorescent irradiation pattern from the irradiated biological tissue; and
- an evaluating unit disposed in operable communication with said detection device, said evaluating unit configured to calculate the surface form or shape of the biological tissue from the detected fluorescent irradiation pattern.

36. The apparatus as in claim 35, wherein said radiation source comprises a laser.

37. The apparatus as in claim 35, wherein said laser is at least one of frequency-multiplied solid laser, an excimer laser, a gas laser, a frequency-multiplied dye laser.

38. The apparatus as in claim 35, wherein said radiation source comprises a flash lamp.

39. The apparatus as in claim 35, further comprising at least one additional radiation source disposed to irradiate the biological tissue with excitation radiation from a direction different from said first radiation source.

40. The apparatus as in claim 35, further comprising a device disposed downstream of said first radiation source to split said excitation radiation so as to irradiate the biological tissue with excitation radiation from at least two directions.

41. The apparatus as in claim 35, further comprising at least one additional detection device disposed to detect the fluorescent irradiation pattern from the biological tissue.

42. The apparatus as in claim 35, further comprising a light deflection device disposed to deflect the fluorescent irradiation pattern from the biological tissue to said detection device.

43. The apparatus as in claim 35, wherein said irradiation pattern generating device comprises a mask having openings defined therein in a pattern corresponding to said irradiation pattern.

44. The apparatus as in claim 35, wherein said irradiation pattern generating device comprises a glass structure having areas that absorb or scatter the excitation radiation and areas that pass the excitation radiation to the biological tissue in said irradiation pattern.

45. The apparatus as in claim 35, wherein said irradiation pattern generating device comprises an arrangement of diffractive optical elements disposed generally transversely to a beam path of said excitation radiation.

46. The apparatus as in claim 35, wherein said irradiation pattern generating device comprises means for producing an interference pattern on the biological tissue.

47. The apparatus as in claim 35, wherein said irradiation pattern generating device comprises an arrangement of mirrors.

48. The apparatus as in claim 35, wherein said detection device comprises a camera.

49. The apparatus as in claim 35, wherein said radiation source is additionally configured for generating radiation suitable for a subsequent operative treatment of the biological tissue.

50. The apparatus as in claim 49, wherein said radiation source is configured for subsequent removal of at least portions of the biological tissue.

51. The apparatus as in claim 35, further comprising an intensity attenuating device disposed between said radiation source and the biological tissue.

52. The apparatus as in claim 35, further comprising a beam widener disposed between said radiation source and the biological tissue.

53. The apparatus as in claim 35, wherein the biological tissue is an eye, and further comprising a eye-tracker device disposed to determine the position of the eye for adjusting said irradiation pattern of excitation radiation onto the eye.

54. The apparatus as in claim 53, wherein said eye-tracker device determines the position of the eye before irradiation of the eye with said excitation radiation.

55. The apparatus as in claim 54, wherein said eye-tracker device also determines the position of the eye after detection of the fluorescent irradiation pattern.

56. The apparatus as in claim 53, wherein said eye-tracker device determines the position of the eye during irradiation of the eye with said excitation radiation and during detection of the fluorescent irradiation pattern.

57. The apparatus as in claim 35, wherein the biological tissue is an eye, and further comprising a laser to subsequently reshape at least of portion of the eye based upon the form or shape of the eye determined by said evaluating unit.

58. The apparatus as in claim 57, wherein said radiation source also comprises said laser for reshaping the eye.

* * * * *